(12) United States Patent
Zwanckaert et al.

(10) Patent No.: US 12,036,100 B2
(45) Date of Patent: Jul. 16, 2024

(54) APPARATUS FOR MAKING AIR-LAID FIBROUS ARTICLES

(71) Applicants: ONTEX BV, Buggenhout (BE); ONTEX GROUP NV, Erembodegem (BE)

(72) Inventors: Danny Zwanckaert, Maldegem (BE); Evan Descheemaecker, Zomergem (BE)

(73) Assignees: Ontex BV, Buggenhout (BE); Ontex Group NV, Erembodegem (BE)

(*) Notice: Subject to any disclaimer, the term of this patent is extended or adjusted under 35 U.S.C. 154(b) by 793 days.

(21) Appl. No.: 17/055,684

(22) PCT Filed: Dec. 6, 2018

(86) PCT No.: PCT/EP2018/083786
§ 371 (c)(1),
(2) Date: Nov. 16, 2020

(87) PCT Pub. No.: WO2019/219228
PCT Pub. Date: Nov. 21, 2019

(65) Prior Publication Data
US 2021/0186768 A1    Jun. 24, 2021

(30) Foreign Application Priority Data

May 18, 2018   (EP) .................... 18173368

(51) Int. Cl.
*A61F 13/15*      (2006.01)
*A61F 13/53*      (2006.01)

(52) U.S. Cl.
CPC ........ *A61F 13/15626* (2013.01); *A61F 13/53* (2013.01); *A61F 2013/15943* (2013.01)

(58) Field of Classification Search
CPC ............... A61F 13/15626; A61F 13/53; A61F 2013/15943
See application file for complete search history.

(56) References Cited

U.S. PATENT DOCUMENTS

| | | | |
|---|---|---|---|
| 4,674,966 A | | 6/1987 | Johnson et al. |
| 2013/0276275 A1* | | 10/2013 | Ishikawa ................. A61F 13/53 28/103 |

FOREIGN PATENT DOCUMENTS

| | | |
|---|---|---|
| DE | 19823954 A1 | 12/1999 |
| EP | 0226939 A2 | 7/1987 |

(Continued)

OTHER PUBLICATIONS

Messler, "Integral Mechanical Attachment", Chapter 3, "Rigid Integral Mechanical Attachments or Interlocks", Elsevier Inc., 2006. (Year: 2006).*

(Continued)

*Primary Examiner* — Christopher W Raimund
(74) *Attorney, Agent, or Firm* — VIVICAR Law, PLLC

(57) ABSTRACT

The present invention relates to an apparatus and a method for making air-laid fibrous articles, as well as absorbent hygiene products comprising such air-laid fibrous articles as absorbent core. It comprises a plurality of discrete pockets (1) defining the shape of the articles disposed in a circumferential relationship about the periphery of a rotatable deposition drum (50) comprising a disk-shaped backing plate (2), characterized in that the discrete pockets (1) are removably attached to interfacing segments (6) which are themselves removably attached to the backing plate (2). The present invention aims to provide an easier and quicker way of interchanging the pockets and to provide an improved handling of different pocket sizes.

9 Claims, 5 Drawing Sheets

(56) References Cited

FOREIGN PATENT DOCUMENTS

| EP | 2623656 | A1 | 8/2013 |
|----|---------|----|--------|
| WO | 9960964 | A1 | 12/1999 |

OTHER PUBLICATIONS

International Search Report and Written Opinion for PCT/EP2018/083786, mailed Feb. 28, 2019.

\* cited by examiner

APPARATUS FOR MAKING AIR-LAID FIBROUS ARTICLES

CROSS-REFERENCE TO RELATED APPLICATIONS

This application is the national stage application of corresponding international application number PCT/EP2018/083786, filed Dec. 6, 2018, which claims priority to and the benefit of European application no. 18173368.4, filed May 18, 2018, which are hereby incorporated by reference in their entireties.

TECHNICAL FIELD

The present invention relates to an apparatus and a method for making air-laid fibrous articles, as well as absorbent hygiene products comprising such air-laid fibrous articles as absorbent core.

Air-laid structures are widely used in the art of absorbent articles and other arts in which fibrous webs are of use. Disposable absorbent hygiene products such as sanitary napkins, diapers, and adult incontinence products commonly employ air-laid fibrous articles as absorbent core, to collect and contain blood, menses, urine and/or vaginal fluids.

BACKGROUND

One common approach for creating air-laid fibrous articles is to process a fibrous sheet of cellulosic fibers or other suitable fibers through a device that breaks up the fibrous sheet, thereby forming discrete fibers. The discrete fibers are entrained in a stream of air and directed to a foraminous forming surface upon which the fibers are deposited to form fluff. Typically, fluff has a high porosity and is comprised of essentially randomly oriented fibers. Generally, a vacuum is applied to one side of the foraminous surface to create a pressure differential across the foraminous forming surface to assist with drawing the discrete fibers to the foraminous forming surface.

Absorbent articles such as sanitary napkins, diapers, and adult incontinence products commonly employ air-laid structures in or as their absorbent core. Absorbent cores have a generally planar structure in which the thickness is generally smaller than the planar dimensions. One common approach to forming air-laid absorbent articles is to situate the foraminous surface in a recess. In the art, the structure in which the foraminous surface is emplaced and the foraminous surface itself are components of what is commonly referred to as a "pocket", sometimes also called "insert" or "mould". The thickness of the absorbent core can be partially controlled by the depth of the recess in the pocket and the planar dimensions of the absorbent core can be defined by the dimensions of the recess and the foraminous surface. The pocket thus defines the shape of the air-laid article desired, whether that shape be rectangular, oval, hourglass, or any other desired shape. After passing under scarfing rolls, which remove excess fluff, the pocket moves to an area where it is shielded from vacuum, and the article formed therein is removed and any wrapping or inclusion between other elements further accomplished. Ideally, a group of pockets are assembled in the shape of a wheel, also called "drum", so that the process of thus forming the air-laid fibrous articles can be continuous. In addition to forming the proper outline of the article, the pocket can be constructed so as to form an article which is thicker in some areas and thinner in others, so that more material is deposited where needed and less where it is not needed.

U.S. Pat. No. 4,674,966 for example discloses such kind of apparatus and process. It discloses an apparatus for forming fibrous pads in the shape in which they will be used, without the need for later cutting, as well as fibrous pads having varied thickness over their surface. It also describes the use of interchangeable inserts, i.e. pockets, said inserts being removably attached to a backing plate of the wheel by means of pegs secured perpendicularly to said backing plate near the edge of said backing plate, which pegs extend through recesses in the matching sidewalls of adjoining inserts.

Although U.S. Pat. No. 4,674,966 discloses removable/interchangeable pockets, it does not explain the advantages of having pockets which are removable/interchangeable. However it is known that pockets may have a limited lifetime and that they sometimes need to be cleaned and replaced partially or totally. For example, pockets may include a perforated screen (e.g. a wire mesh or a micro-perforated screen) at the bottom of the recess, above the foraminous surface, preferably having a pore dimension which is less than the foraminous surface. It allows to hold the smaller material components of the fibrous article within the pocket, avoiding that they become sucked by the vacuum applied through the porous, air permeable, foraminous bottom surface of the pocket. Such perforated screen may need to be replaced, and this can be done more easily if each pocket can be easily removed from the drum, then easily replaced on the drum once the screen has been changed.

More and more, there is a need for a single manufacturing line to be able to manufacture different shapes and sizes of air-laid fibrous articles, and thus work with different sizes of pockets: shorter to longer, for example for producing sanitary napkins going from size MINI up to size NIGHT. Currently, to change from one size of a product to another size, it is common practice to change the whole drum and associated set of pockets to another drum having a different associated set of pockets. The reason for that is that it is not possible to fix different pockets having different lengths with the same attachment means all around the drum. Taking back the example of U.S. Pat. No. 4,674,966, the pegs would need to be positioned differently for each different length of the pockets. And at some point within the wheel circumference, there will always be at least an impossibility, where holes for fixing the pegs will partially overlap between two sizes, thereby avoiding right fixation of the pegs.

However the full change of a drum is a complex and dangerous operation. Indeed a drum can be large, heavy and cumbersome. If a drum is not manipulated very carefully, it can moreover lose its concentricity, thereby leading to the production of air-laid articles which are not stable along production. In addition, various drums are necessary, which is very costly because of the high cost for manufacturing such drums, and they all then need to be stored, which takes a lot of space. Moreover a lot of other pieces around the drum may need to be manipulated, potentially moved or even replaced when changing a drum, e.g. the vacuum casing around the drum, pipes, the fluff feeding channels, scarfing tools, transporting bands, felts, etc.

Alternatively, it is known to use a single drum and adapt the positioning of the different pockets along various circumferences having different diameters, to fit the length of the pockets to a specific drum diameter. But this is again very complex to handle, because it needs adaptation of all the elements around the drum (e.g. the vacuum casing around the drum, pipes, the fluff feeding channels, scarfing tools, transporting bands, felts) to always ensure close fit between these and each possible circumference of the drum. In addition, this embodiment generally cannot cover all the possible pocket sizes on a same drum, but only 2 or 3 different sizes.

There remains thus a need in the art for an improved easier and quicker way of interchanging the pockets on a drum used in an apparatus for continuously making air-laid fibrous articles.

And there remains also a need in the art for an improved handling of different pocket sizes on an apparatus for continuously making air-laid fibrous articles, in particular a handling which is easier, more flexible, cheaper, quicker and safer.

The present invention aims to resolve at least some of the problems mentioned above and thereby aims to provide such easier and quicker way of interchanging the pockets and to provide an improved handling of different pocket sizes.

SUMMARY OF THE INVENTION

The present invention provides an apparatus for forming air-laid fibrous articles, according to claim 1. It comprises a plurality of discrete pockets defining the shape of the articles to be formed, disposed in a circumferential relationship about the periphery of a rotatable deposition drum comprising a disk-shaped backing plate. It is characterized in that the discrete pockets are removably attached to interfacing segments which are themselves removably attached to the backing plate. This overcomes the problems of prior art apparatuses, since the use of interfacing segments may ensure a quicker and easier changeover of various pockets at a same time and/or changeover between pockets of different sizes, whilst keeping the drum in place. So only a set of interfacings segments and corresponding pockets is needed per product size, and not an entire drum.

In a further aspect, according to claim 11, the present invention provides a method for manufacturing absorbent hygiene products such as sanitary napkins, diapers, and adult incontinence products, comprising an absorbent core manufactured with an apparatus according to the present invention.

In still a further aspect, according to claim 12, the present invention provides absorbent hygiene products such as sanitary napkins, diapers, and adult incontinence products, comprising an absorbent core manufactured with an apparatus according to the present invention.

Other objects and advantages of this invention will become apparent hereinafter.

DETAILED DESCRIPTION OF THE INVENTION

Very generally, and as known in the art, in a process for forming air-laid fibrous articles, firstly a web of compressed fibrous material is fed into a hammermill, fiberized, and fibers entrained in an air stream caused by a vacuum source. The air stream draws these fibers, forming together the fluff, down onto depressions on the upper surfaces of pockets, which are partially foraminous, in the shape, contour and thickness of the air-laid fibrous article desired.

Figure 1A:
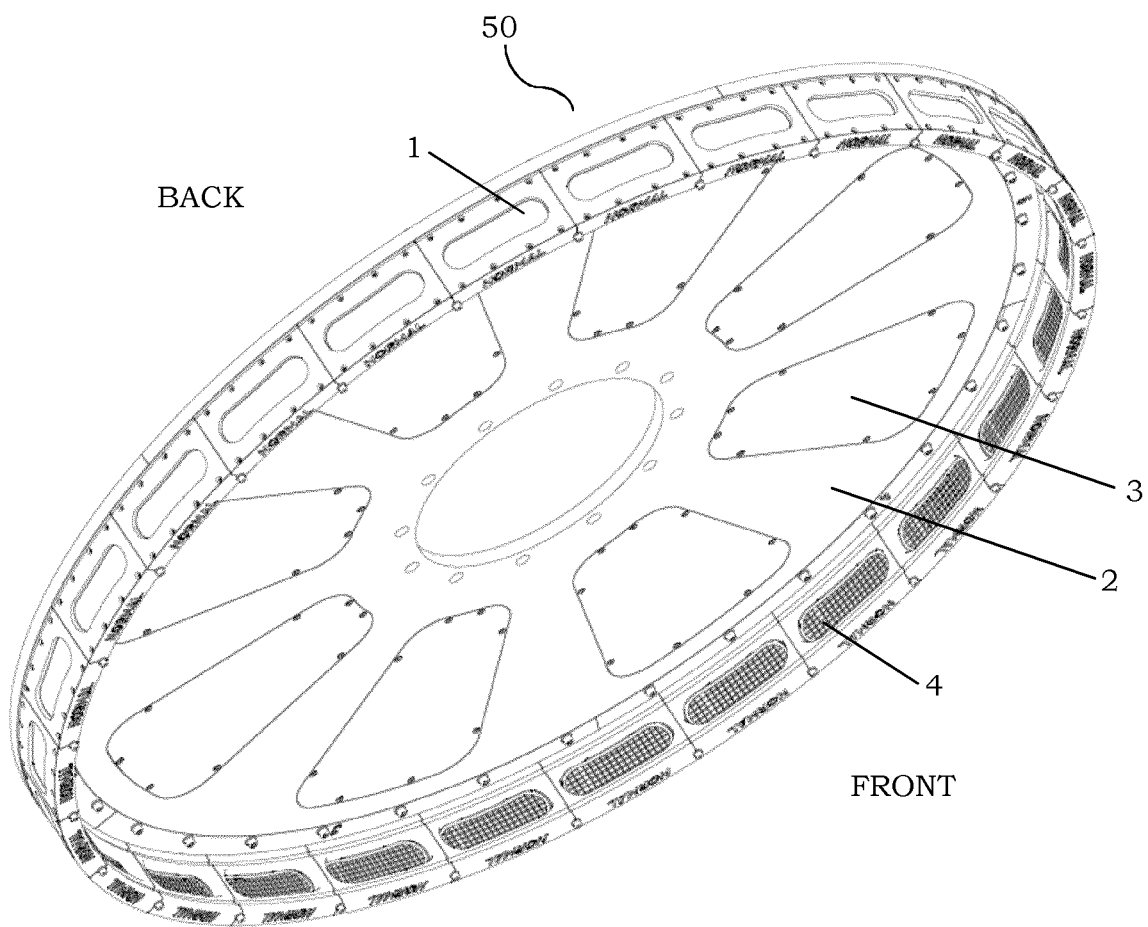
FIG. 1A shows a perspective overview of an apparatus according to the present invention.
Figure 1B:
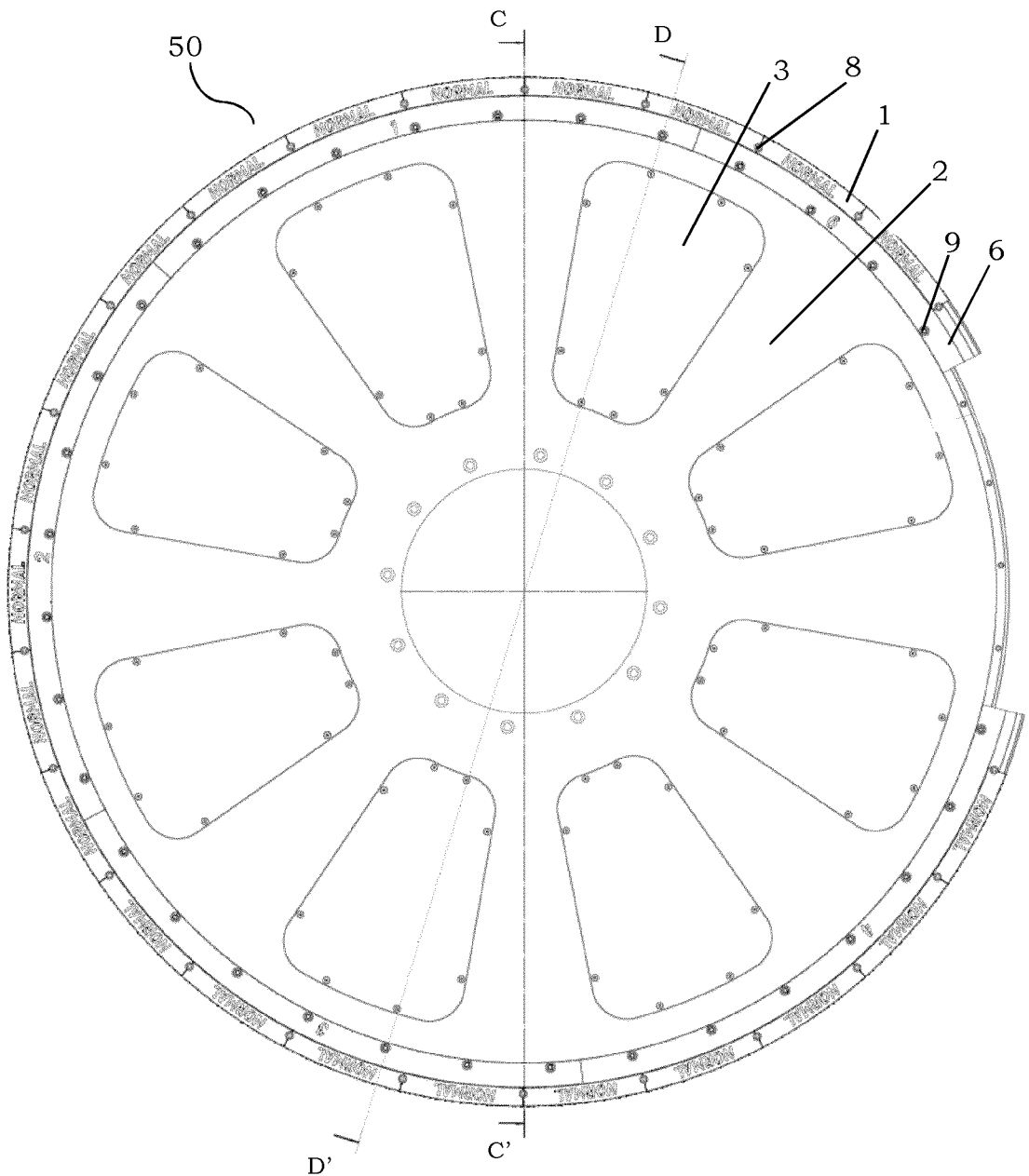
FIG. 1B shows a front view of the apparatus of FIG. 1A, partially cut away.

As can be seen from FIG. 1, each pocket 1 is arcuately shaped and together with a number of identical pockets, form a drum 50. The pockets 1 are fixed to a disk-shaped backing plate 2.

Generally, the path of vacuum is from the hammermill, through the pockets, and is then turned toward the back of the apparatus (that is, away from the viewer in FIG. 1B), passing through openings 3 in the backing plate 2. Referring to the path of the fluff, the vacuum draws the fluff down from the hammermill to be deposited on the foraminous surface 4 of the pockets 1, as the vacuum passes through this foraminous surface and exits the back of the machine as explained above. A vacuum casing (not shown) encases the major portion of the drum, except in an arc sector area, generally in the form of a "slice of pie" area, where the pocket is shielded from vacuum, and the article formed therein can be removed.

Figure 2:
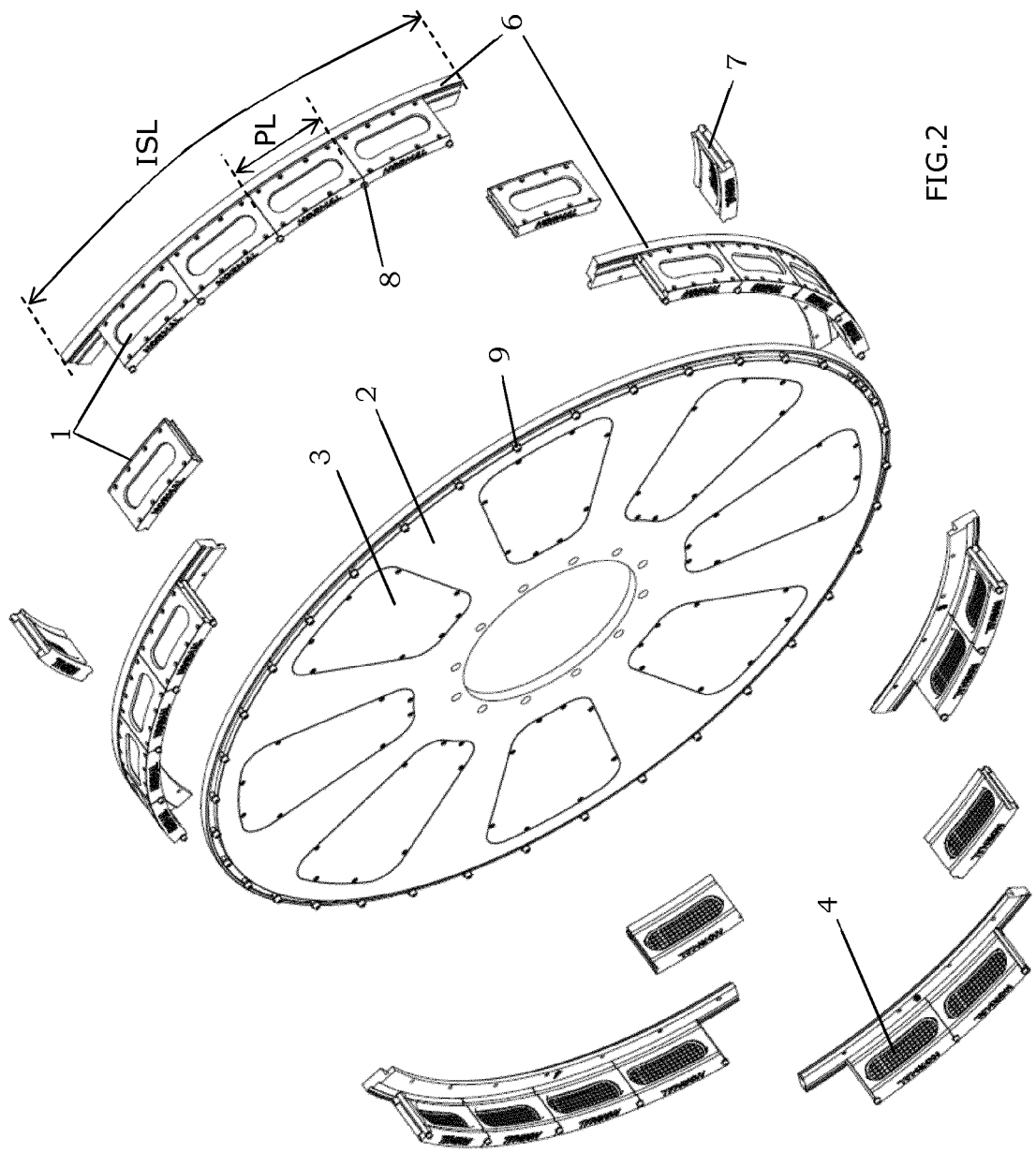
FIG. 2 shows an exploded overview of the apparatus of FIG. 1A.

In an advantageous embodiment of the present invention, the pockets are removably attached to interfacing segments by primary attachment means, the distance between two adjacent primary attachment means being dependent on the pocket length (PL). These primary attachment means can be any suitable means. One preferable means, shown herein in FIG. 2, is to thread rods 5 into interfacing segments 6. Pockets 1 may then be formed with a matching semi-cylindrical groove 7 in each end. The spacing of rods 5 about interfacing segments 6 is such that each pocket 1 fits tightly between its respective rods. The length of each rod should be nearly but no greater than the width of the pockets. After each pocket is slid between its respective rods (see FIG. 3), a bolt 8 is tightened into the outer end of each rod to hold each pocket tightly in position. Alternatively the pockets could be simply bolted to interfacing segments 6 or affixed in any other secure but removable manner.

Speaking in more general terms, the pockets 1 may advantageously be defined by longitudinal sidewalls 20 and transversal sidewalls 21, said transversal sidewalls having recesses 7, an air impervious top surface 22 and a foraminous surface 4 recessed below said air impervious top surface such that said top surface surrounds and defines two dimensions of the shape of the article to be formed, the distance by which the foraminous surface is below the top surface defining the third dimension, and said pockets 1 may be removably attached to said interfacing segments 6 by means of fastening rods 5 secured perpendicularly to said interfacing segments, which rods extend through said recesses 7 in the matching transversal sidewalls 21 of adjoining pockets 1. Then, preferably, the pockets 1 may be hold in position by bolts 8 screwed into the fastening rods 5.

Preferably, the interfacing segments 6 are removably attached to the backing plate 2 by secondary attachment means 9, the distance between two adjacent secondary attachment means being independent on the pocket length (PL). For example, the interfacing segments 6 may be hold in position by bolts 9 screwed into the backing plate 2.

Figure 3:
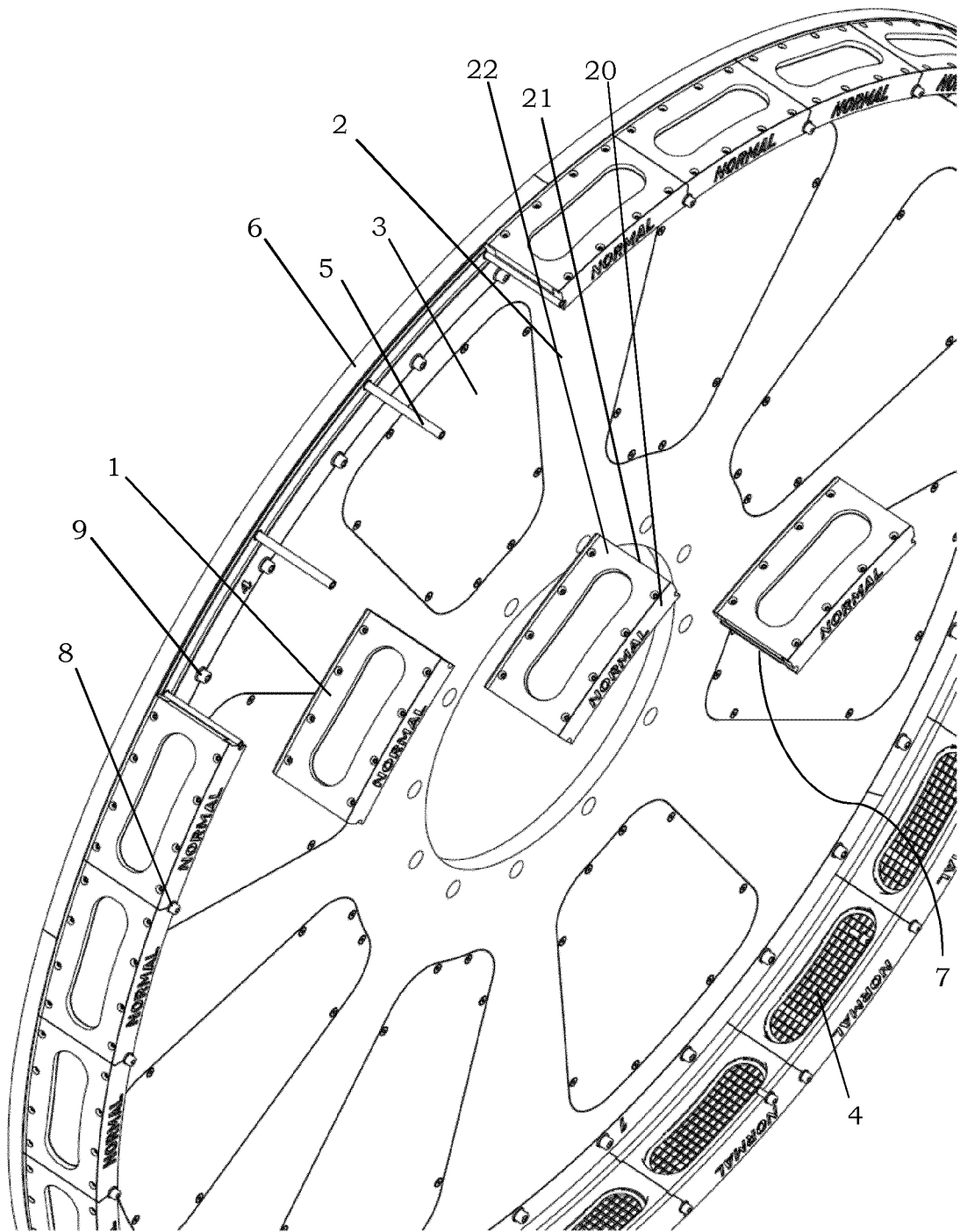
FIG. 3 is a detail of another partially exploded overview of the apparatus of FIG. 1A.

When a switch between pockets of the same length has to be done, for example to clean or replace part of a pocket or an entire pocket, or alternatively to switch between pockets having different shapes (e.g. hourglass vs. rectangular) or different depths (e.g. for manufacturing thinner or thicker air-laid fibrous articles), but still the same length, an apparatus according to the present invention may show the advantage that only the pockets need to be swapped, whilst the interfacing segments remain affixed to the backing plate (see FIG. 3).

When a switch between pockets of a different length has to be done, for example for an article size change (different length of the air-laid fibrous article), an apparatus according to the present invention may show the advantage that only the interfacing segments together with their pockets need to be changed (see FIG. 2), and not the entire drum.

So in no case, the drum has to be manipulated or changed, thereby avoiding complex and dangerous operation, avoiding the risk of losing concentricity, avoiding the need for space to store various drums, avoiding to pay the cost of manufacturing various drums, avoiding the handling of all the pieces around the drum, and avoiding the adaptations needed when using drums with varying circumference.

We have found that without the use of interfacing segments, it was not possible to fit multiple sizes (i.e. pockets lengths) onto a single backing plate, because some drilled fixation holes needed for fixing the rods to the backing plate started to partially overlap improperly. The use of an apparatus according to the present invention solves this problem and may ensure a quick changeover between both different products having the same length or different products having a different length.

In a preferred embodiment, the drum 50 comprises at least two interfacing segments 6, of which at least one comprises more than one discrete pocket 1. Having less interfacing segments and ensuring that at least one interfacing segment bears more than one pocket may decrease the changeover time when an article size change has to be done. More preferably, the drum comprises at least 3, or at least 4, or at least 5 interfacing segments. The number of interfacing segments may be dependent on the length of the interfacing segments and the size (i.e. circumference) of the drum. Preferably, an interfacing segment comprises at least 2, or at least 3, or at least 4 discrete pockets. The number of pockets on an interfacing segment may be dependent on the length of the interfacing segments and the length of the pockets.

We have found that the present invention was particularly advantageous for larger drums, e.g. drums having a diameter of at least 1.5 m, which comprise more pockets, e.g. more than 15 pockets. This is because it is easier to keep more or less the same diameter of the drum, whatever the length of the pockets is. The difference of only a few millimeters may then be easily compensated by product transport settings downstream the drum. As an example, a drum with a diameter of about 2 m, used for the manufacture of the absorbent core of sanitary napkins, may comprise 21 pockets of the size NIGHT, 22 of the size SUPER, 26 of the size NORMAL, 29 of the size SHORT and 34 of the size MINI.

Advantageously, the arc length of the interfacing segments (ISL) is smaller than the arc length of the area of the drum which is not encased in the vacuum casing. As already explained a vacuum casing encases the major portion of the drum, except in an arc sector area, generally in the form of a "slice of pie" area, where the pocket is shielded from vacuum, and the article formed therein can be removed. If the length of the interfacings segments is smaller than this opening, said segments may easily be removed and replaced, without the need for switching the vacuum off, opening the vacuum casing, then reclosing the vacuum casing and waiting the vacuum to be appropriate again to restart production. The drum can easily be rotated, to allow access to each intermediate segment of the circumference.

A practical example of a changeover of the interfacing segments can be described with the help of FIG. 2, which shows a drum with a diameter of about 2 m, used for the manufacture of the absorbent core of sanitary napkins of the size NORMAL, comprising 26 pockets and 6 interfacing segments. Four interfacing segments each carry 4 pockets, and two other interfacing segments each carry 2 pockets; finally, 6 pockets are sitting across the junctions between the individual interfacing segments. A first pocket, covering the junction between two interfacing segments, is slid out of its fixation rods, and the other pocket covering the junction between two interfacing segments at the opposite side of the same interfacing segment is also slid out, thereby rendering said in between interfacing segment (always wearing its pockets) free to be unbolted and exchanged with another interfacing segment (wearing pockets of a different size), using the same attachment means (same bolts and holes). The drum is then turned until the next junction between two interfacing segments. There the pocket covering said junction is slid out and the next interfacing segment is removed and replaced. A new pocket can then be slid in and fixed, between the two newly replaced interfacing segment. The drum is then again turned until the next junction between two interfacing segments and the same operations are performed, until a last new pocket is slid in and fixed, between the last newly replaced interfacing segment and the first replaced interfacing segment. Although the replacement of an entire drum can generally take from 6 hours up to 2 days, depending on the configuration, the changeover according to the present invention can take between 10 and 30 minutes, which is highly advantageous. Moreover, as also apparent from FIG. 2, storing a few interfacing segments and pockets instead of an entire drum is much more convenient.

As described in this example and shown in FIG. 2, it is preferred that a discrete pocket straddles two contiguous interfacing segments, so that the rods for fixing the pockets to the interfacing segments are fully included into the material of the interfacing segments. This may ensure good fixation and tight fit.

In a preferred embodiment, the apparatus according to the present invention further comprises primary tongue and groove positioning means between the pockets and the interfacing segments. This may help ensuring a tight fit between the pockets and the interfacing segments. Indeed we have noticed that the prior art use of rods only to center and fix the pockets to the backing plate of a drum (as in U.S. Pat. No. 4,674,966 for example) may lead to problems of loss of concentricity, i.e. roundness, of the drum, thereby leading to problems of stability of product manufacturing. The use of primary tongue and groove positioning means according to the present invention may solve this problem. It may also reduce the passageway of air from the exterior of the vacuum casing to said vacuum casing.

In another preferred embodiment, the apparatus according to the present invention further comprises secondary tongue and groove positioning means between the interfacing segments and the backing plane. This may help ensuring a tight fit between the interfacing segments and the backing plate, ensuring drum's concentricity and/or reducing the passageway of air.

Still more preferably the apparatus according to the present invention comprises both primary and secondary tongue and groove positioning means.

Figure 4:
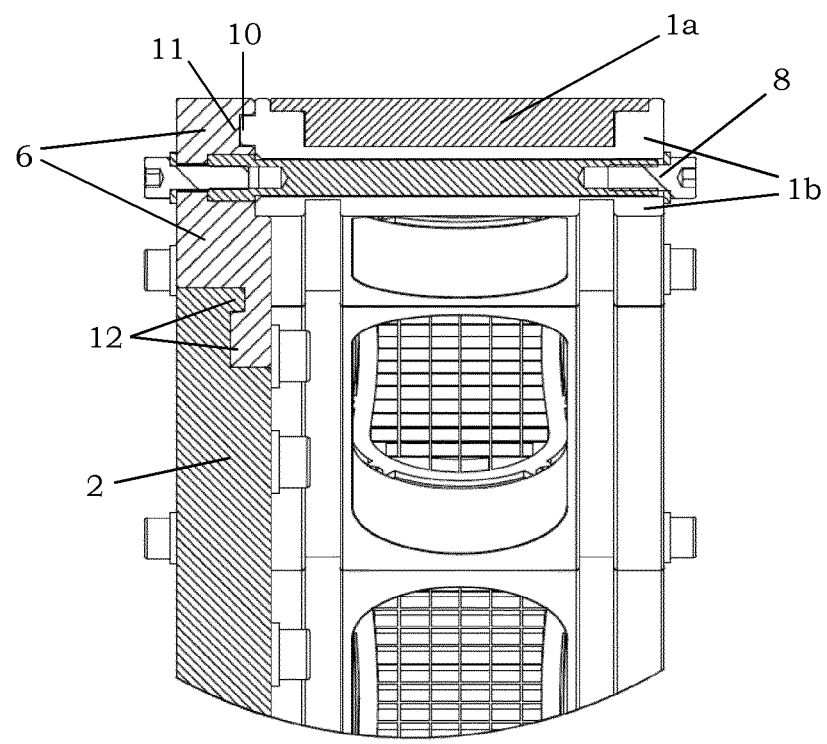
FIG. 4 is a sectional view of a detail of FIG. 1B taken along line C-C', in the periphery of the apparatus, close to C.

Exemplary FIG. 4, which illustrates a cross-section at a junction between two pockets, shows a pocket made of two pieces: a cover 1a and a base 1b. The base of the pocket has a transversal sidewall (that is, facing the viewer of FIG. 4) having a recess in the form of a semi-cylindrical groove, through which a fastening rod 5 extends. The fastening rod 5 is secured perpendicularly to the interfacing segment 6, and the pockets is hold in position by bolt 8 screwed into the fastening rod 5. The base of the pocket further comprises a tongue 10, adapted to fit into a corresponding groove 11 within the interfacing segment 6. Also visible on this figure, are the secondary tongue and groove positioning means 12 between the interfacing segment 6 and the backing plane 2.

Figure 5:
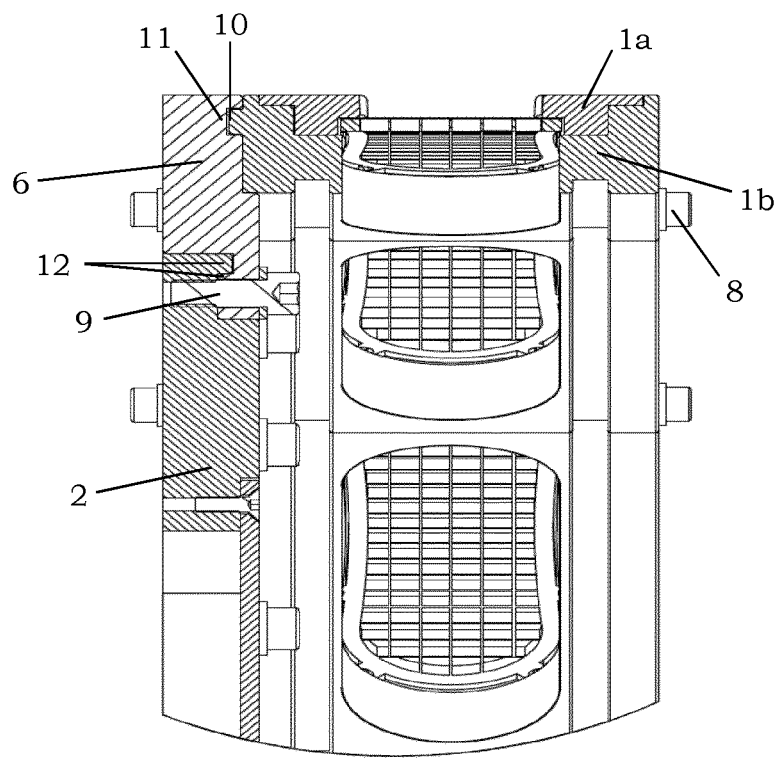
FIG. 5 is a sectional view of a detail of FIG. 1B taken along line D-D', in the periphery of the apparatus, close to D.

Exemplary FIG. 5 illustrates a cross-section within a pocket 1a-1b, across a secondary attachment means 9 used to removably attach the interfacing segment 6 to the backing plate 2. Also visible on this figure, are the primary tongue and groove positioning means 10-11 between the pocket base 1b and the interfacing segment 6 and the secondary tongue and groove positioning means 12 between the interfacing segment 6 and the backing plane 2.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

"Absorbent article" refers to devices that absorb and contain liquid, and more specifically, refers to devices that are placed against or in proximity to the body of the wearer to absorb and contain the various exudates discharged from the body. Absorbent articles include but are not limited to diapers, adult incontinence briefs, training pants, diaper holders and liners, sanitary napkins and the like, as well as surgical bandages and sponges. Absorbent articles preferably comprise a longitudinal axis and a transversal axis perpendicular to said longitudinal axis. The longitudinal axis is hereby conventionally chosen in the front-to-back direction of the article when referring to the article being worn, and the transversal axis is conventionally chosen in the left-to-right direction of the article when referring to the article being worn. Disposable absorbent articles can include a liquid pervious top sheet, a back sheet joined to the top sheet, and an absorbent core positioned and held between the top sheet and the back sheet. The top sheet is operatively permeable to the liquids that are intended to be held or stored by the absorbent article, and the back sheet may or may not be substantially impervious or otherwise operatively impermeable to the intended liquids. The absorbent article may also include other components, such as liquid wicking layers, liquid intake layers, liquid distribution layers, transfer layers, barrier layers, wrapping layers and the like, as well as combinations thereof. Disposable absorbent articles and the components thereof can operate to provide a body-facing surface and a garment-facing surface.

The "absorbent medium" or "absorbent core" or "absorbent body" is the absorbent structure disposed between the top sheet and the back sheet of the absorbent article in at least the crotch region of the absorbent article and is capable of absorbing and retaining liquid body exudates. It may be manufactured in a wide variety of shapes (for example, rectangular, trapezoidal, T-shape, I-shape, hourglass shape, etc.) and from a wide variety of materials. Examples of commonly occurring absorbent materials are cellulosic fluff pulp, tissue layers, highly absorbent polymers (so called superabsorbent polymer particles (SAP)), absorbent foam materials, absorbent nonwoven materials or the like. It is common to combine cellulosic fluff pulp with superabsorbent polymers in an absorbent material. The absorbent core can include one or more liquid absorbent layers.

The term "consisting essentially of" does not exclude the presence of additional materials which do not significantly affect the desired characteristics of a given composition or product. Exemplary materials of this sort would include, without limitation, pigments, antioxidants, stabilizers, surfactants, waxes, flow promoters, solvents, particulates and materials added to enhance processability of the composition.

"Longitudinal" is a direction running parallel to the maximum linear dimension of the article.

"Pulp fluff" or "fluff pulp" refers to a material made up of cellulose fibers. The fibers can be either natural or synthetic, or a combination thereof. The material is typically lightweight and has absorbent properties.

The term "sanitary napkin", as used herein, refers to an article which is worn by females adjacent to the pudendal region that is intended to absorb and contain the various exudates which are discharged from the body (e.g., blood, menses, and urine).

As used herein, the term "transverse" or "lateral" refers to a line, axis, or direction which lies within the plane of the absorbent article and is generally perpendicular to the longitudinal direction.

By the term "wrapping material", "wrapping" or "wrapping layer" as used herein, is meant a bendable material, preferably a sheet material of which the thickness is smaller, more preferably much smaller than its width or length, such as a sheet, a film or a foil. In a particularly preferred embodiment, said wrapping material is capable of being rolled up. An absorbent core, in particular an absorbent core comprising superabsorbent particles, preferably comprises a "wrap" or "wrap sheet" or "wrapping layer" so as to prevent the absorbent material and superabsorbent particles from escaping from the finished product.

The invention was described by the hereinabove non-limiting examples which illustrate the invention, and are not intended to, nor should they be interpreted to, limit the scope of the invention. It is supposed that the present invention is not restricted to any form of realization described previously and that some modifications can be added to the presented example of fabrication without reappraisal of the appended claims.

The invention claimed is:

1. An apparatus for forming air-laid fibrous articles, comprising a plurality of discrete pockets (1) defining the shape of the articles disposed in a circumferential relationship about the periphery of a rotatable deposition drum (50) comprising a disk-shaped backing plate (2), characterized in that the discrete pockets (1) are removably attached to interfacing segments (6) which are themselves removably attached to the backing plate (2), wherein the pockets (1) are defined by longitudinal sidewalls (20) and transversal sidewalls (21), said transversal sidewalls having recesses (7), an air impervious top surface (22) and a foraminous surface (4) recessed below said air impervious top surface such that said top surface surrounds and defines two dimensions of the shape of the article to be formed, the distance by which the foraminous surface is below the top surface defining the third dimension, said pockets (1) being removably attached to said interfacing segments (6) by means of fastening rods (5) secured perpendicularly to said interfacing segments (6), which rods extend through said recesses (7) in the matching transversal sidewalls (21) of adjoining pockets (1), and wherein a discrete pocket straddles two contiguous interfacing segments.

2. An apparatus according to claim 1, wherein the drum (50) comprises at least two interfacing segments (6), of which at least one comprises more than one discrete pocket (1).

3. An apparatus according to claim 1, wherein the discrete pockets (1) are removably attached to the interfacing segments by primary attachment means (5), the distance between two adjacent primary attachment means being dependent on the pocket length (PL).

4. An apparatus according to claim 1, wherein the pockets (1) are held in position by bolts (8) screwed into the fastening rods (5).

5. An apparatus according to claim 1, wherein the interfacing segments (6) are removably attached to the backing plate (2) by secondary attachment means (9), the distance between two adjacent secondary attachment means being independent on the pocket length (PL).

6. An apparatus according to claim 1, further comprising primary tongue and groove positioning means (10,11) between the pockets (1) and the interfacing segments (6).

7. An apparatus according to claim 1, further comprising secondary tongue and groove positioning means (12) between the interfacing segments (6) and the backing plate (2).

8. An apparatus according to claim 1, comprising a vacuum casing encasing the major portion of the drum, except in an arc sector area, wherein the arc length of the interfacing segments (ISL) is smaller than the arc length of said arc sector area of the drum which is not encased in the vacuum casing.

9. A method for manufacturing absorbent hygiene products comprising:
   providing an apparatus according to claim 1,
   forming air-laid fibrous articles with said apparatus,
   incorporating said air-laid fibrous articles as absorbent core in the absorbent hygiene products.

* * * * *